(12) United States Patent
Santar et al.

(10) Patent No.: US 6,596,791 B2
(45) Date of Patent: Jul. 22, 2003

(54) POLYMER COMPLEXES OF GLUCURONOGLUCANES

(75) Inventors: Ivan Santar, Predklasteri (CZ); Frantisek Kiss, Brno (CZ); Jiri Briestensky, Cernilov (CZ)

(73) Assignee: Alpenstock Holdings Limited, Sallynoggin (IE)

( * ) Notice: Subject to any disclaimer, the term of this patent is extended or adjusted under 35 U.S.C. 154(b) by 21 days.

(21) Appl. No.: 09/764,346

(22) Filed: Jan. 19, 2001

(65) Prior Publication Data

US 2003/0040487 A1 Feb. 27, 2003

Related U.S. Application Data

(63) Continuation of application No. PCT/IE99/00067, filed on Jul. 21, 1999.

(30) Foreign Application Priority Data

| Jul. 21, 1998 | (IE) | S980594 |
| Jul. 21, 1998 | (IE) | S980595 |
| Jul. 21, 1998 | (IE) | S980596 |
| Jul. 21, 1998 | (IE) | S980597 |
| Jul. 21, 1998 | (IE) | S980598 |
| Jul. 21, 1998 | (IE) | S980599 |

(51) Int. Cl.$^7$ .............. C08J 5/10; C08L 3/00; C08L 89/00
(52) U.S. Cl. .............. 524/47; 524/35; 524/38
(58) Field of Search .............. 524/35, 37, 38, 524/39, 40, 47, 56

(56) References Cited

U.S. PATENT DOCUMENTS

| 4,100,341 A | 7/1978 | Brasey et al. ........ 536/56 |
| 5,166,137 A | 11/1992 | Otterlei et al. ........ 514/23 |
| 5,785,994 A | * 7/1998 | Wong et al. ........ 424/473 |

FOREIGN PATENT DOCUMENTS

| EP | 0659440 A1 | 6/1995 |
| WO | WO98/00180 | 1/1998 |
| WO | WO98/33822 | 8/1998 |

OTHER PUBLICATIONS

Michaeli et al, Science, vol. 166, "Localization of Antigenic Determinants in the . . . ", pp. 1522–1523, Dec. 1969.
Abstract of Czech Republic Patent No. 870415, XP–002120226.
Database WPI Week 197612, Derwent Publications Ltd., "Capsules with strong wall . . . ", & JP51014179A (Fuji . . . ), Feb. 4, 1976.
Yacket et al, Kodak Research Lab., vol. 64, "The Oxidation of Cellulose by . . . ", pp. 121–127, Jan. 1942.
Abstract of Great Britain Patent No. 709684.
Domszy et al, Physical Sciences Dept., Trent Polytechnic, Ionic Interactions Between . . . , pp. 331–336, 1985.
Shorygin Chait, E.V.: Zh. obshch. Chim. 7, p. 188, 1937.

* cited by examiner

*Primary Examiner*—James J. Seidleck
*Assistant Examiner*—U. K. Rajguru
(74) *Attorney, Agent, or Firm*—Jacobson Holman PLLC

(57) ABSTRACT

A biocompatible intermolecular polymer complex comprises an anionic component and a non protein cationic component. The anionic component comprises a linear or branched polysaccharide chain wherein at least 5% of the basic structural units are glucuronic acid. The cationic component comprises a linear or branched natural, semi-synthetic or synthetic oligomer or polymer.

33 Claims, No Drawings

1

POLYMER COMPLEXES OF GLUCURONOGLUCANES

This appl is a continuation of PCT/IE99/00067 filed Jul. 21, 1999.

INTRODUCTION

Oxidised cellulose and its derivatives have been widely used in medicine and pharmacy since the first preparation by Chait and Kenyon [Shorygin P P., Chait E. V.: Zh. obshch. chim. 7, 188 (1937); Yackel E. C., Kenyon W. O.: J Am. Chem. Soc. 64, 121 (1942)].

Other types of haemostatics and antifibrinolytics have been introduced, however, oxidised cellulose especially in the highly pure form of a polyanhydroglucuronic acid and their copolymers (PAGA), and notably salts thereof, is used in various medicinal applications as a completely resorbable semi-synthetic polymer with minimum adverse effects in the organism. This is true for both the basic substance prepared according to GB 709684; U.S. Pat. No. 4,100,341, or salts thereof prepared according to more recent patents, such as.: CS AO 242920; EP 0659440A1 and PCT IE 98/00004.

It is known that after application of oxidised cellulose to stop surface bleeding a rigid scab is formed, especially on movable parts of the body, such as knees, fingers or ankles. This may be a disadvantage because it can crack and lead to renewed bleeding. Using a haemostat according to PCT IE 98/00004 this disadvantage can be partially overcome by altering the technological conditions of the manufacture (such as increasing the amount of crosslinks) which brings about increased accumulation of the body fluids in the substance and thereby the flexibility of the wound cover is optimised.

Within the last two decades, during investigations of various types of polysaccharides, it was established that during their biodegradation in the living organism certain functions of various types of cells are influenced. [Berger J., Nemec J., Sedlmayer P., Vortel V.: Report on Toxicological Investigation of a New Drug Preparation "Mikrocel", Internal report, Research Institute for Pharmacy and Biochemistry, Praha, branch Pardubice-Rosice and Labem, 1984; Burchard W.: Polysacharide, Eigenschaften und Nutzung, Springer-Verlag, Berlin, Heidelberg, New York, Tokyo, p. 144 (1985); U.S. Pat. No. 5,166,137]. Depending on the type of bond in the main glycosydic chain, on the value of the degree of polymerisation, on the presence of various functional groups, and the degree of ionisation thereof, on the type of structural units, and the type of salt or a complex salt thereof, these polysaccharides affect the immune system of the organism. It seems for instance that glucanes bonded by an 1,3 β bond have immunomodulative properties while 1,4 β bonded glucanes suppress tumorous growth. There are however exceptions to these rules. An important factor underlying these properties is the presence of the glucuronic acid in the chain.

It is known that a large proportion of bonds between individual substances occurring in living organisms is of a non-covalent nature, such as hydrogen bonds, van der Waals forces, or bonds of an ionic character especially with biopolymers. These bonds create so-called intermolecular polymeric complexes (IMC) such as for example, heparin-peptides. In general these complexes represent a new class of macromolecular substances formed by association of individual polymer chains into macromolecules through secondary bonding interactions. According to the nature of the interactions these complexes can be subdivided into polyelectrolyte complexes, hydrogen bonded complexes, stereo complexes and charge transfer complexes. These types of complexes have a number of common properties, notably an organised supermolecular structure and the ability to create other higher supermolecular entities. The characteristic feature is their ability to undergo restructuring depending on the conditions prevailing in their environment. Further they are capable of undergoing interpolymer substitution reactions and it is especially due to this latter ability that the IMCs in their behaviour come close to imitating biochemical processes occurring in living organisms.

The invention in particular involves the use of polyanhydroglucuronic acids and salts thereof. The term polyanhydroglucuronic acid and salts there of as used herein also includes copolymers thereof, especially with anhydroglucose. This is hereinafter referred to as PAGA.

Co-pending patent application PCT IE98/00004 describes particular polyanhydroglucuronic acids and salts thereof and a method of preparing such compounds. In particular therefore, the term polyanhydroglucuronic acids and salts thereof includes the acids and salts referred to in this co-pending application.

STATEMENTS OF INVENTION

According to the invention there is provided a biocompatible intermolecular polymer complex of:
an anionic component comprising a linear or branched polysaccharide chain wherein at least 5% of the basic structural units are glucuronic acid; and
a non protein cationic component comprising a linear or branched natural, semi-synthetic or synthetic oligomer or polymer.

In a preferred embodiment of the invention the cationic component contains nitrogen that either carries a positive charge or wherein the positive charge is induced by contact with the polysaccharidic anionic component.

In one case the cationic component is selected from derivatives of acrylamide, methacrylamide and copolymers thereof. Preferably the cationic component is selected from polyacrylamide, copolymer of hydroxyethylmethacrylate and hydroxypropylmetacrylamide, copolymers of acrylamide, butylacrylate, maleinanhydride and/or methylmetacrylate.

In another case the cationic component is a cationised natural polysaccharide. Preferably the polysaccharide is a starch, cellulose or gum. The gum may be guargumhydroxypropyltriammonium chloride.

In another case the cationic component is a synthetic or semi-synthetic polyamino acid. Preferably the cationic component is polylysin, polyarginin, or α,β-poly-[N-(2-hydroxyethyl)-DL-aspartamide].

In a further embodiment the cationic component is a synthetic anti-fibrinolytic. The anti-fibrinolytic may be a hexadimethrindibromide (polybren).

In a still further embodiment the cationic component is a natural or semi-synthetic peptide. Preferably the peptide is a protamine, gelatine, fibrinopeptide, or derivatives thereof.

In a further case the cationic component is an aminoglucane or derivatives thereof. Preferably the aminoglucane is fractionated chitin or its de-acetylated derivative chitosan. The aminoglucane may be of microbial origin or is isolated from the shells of arthropods such as crabs.

In a preferred embodiment of the invention the anionic component is polyanhydroglucuronic acid and/or biocompatible salts thereof.

In this case preferably the polyanhydroglucuronic acid and salts thereof contain in their polymeric chain from 8 to 30 percent by weight of carboxyl groups, at least 80 percent by weight of these groups being of the uronic type, at most 5 percent by weight of carbonyl groups, and at most 0.5 percent by weight of bound nitrogen. Preferably the polyanhydroglucuronic acid and salts thereof contain in their polymeric chain at most 0.2 percent by weight of bound nitrogen.

In a preferred embodiment the molecular mass of the polymeric chain of the anionic component is from $1\times10^3$ to $3\times10^5$ Daltons, ideally, the molecular mass of the polymeric chain of the anionic component ranges from $5\times10^3$ to $1.5\times10^5$ Daltons.

Most preferably the content of carboxyl groups is in the range of from 12 to 26 percent by weight, at least 95 percent of these groups being of the uronic type.

In a preferred embodiment of the invention the anionic component contains at most 1 percent by weight of carbonyl groups.

The carbonyl groups are preferably intra- and intermolecular 2,6 and 3,6 hemiacetals, 2,4-hemialdals and C2–C3 aldehydes.

The cationic component may be gelatine.

Alternatively the cationic component is chitosan.

The invention also provides a pharmaceutical or cosmetic composition including at least one biocompatible complex of the invention.

Preferably the composition includes at least one biocompatible biologically active substance.

The composition may alternatively or additionally include at least one biologically acceptable adjuvant.

DETAILED DESCRIPTION

We have now found that by preparing polymeric intermolecular complexes (IMC) of glucoronoglucanes, notably microdispersed PAGA, prepared especially, according to PCT IE 98/00004 it is possible to enhance the haemostatic effect of the final products on this basis and the properties of the temporary wound cover formed after the haemostasis is achieved such as its flexibility and resistance to cracking on movable parts of the body.

It is also possible to upgrade physicomechanical properties of the final products on this basis. Such IMCs make it possible to prepare application forms whose manufacture from a pure PAGA or their simple salts is extremely difficult. Such application forms includes non-woven textile-like structures or polymeric films. To modify or upgrade the physical mechanical properties it is sufficient to use even a relatively small amount of polymeric counterion while it is possible to obtain suitable application properties within a broad concentration range of the components. The ratio of the glucuronoglucane to polymeric counterion can be 0.99:0.01 to 0.01:0.99.

Another advantage of glucuronoglucane based IMCs is the possibility to control their biological properties such as varying the degree of haemostatis, resorption time, or immunomodulative properties, and the like.

Polymeric cations suitable to form IMCs with glucuronoglucanes prepared for example according to PCT IE 98/00004 may roughly be subdivided into the following groups:

1. Synthetic biocompatible nitrogen-containing oligomers and polymers.
   a) Derivatives of acrylamide and methacrylamide and their copolymers [such as polyacrylamide, copolymer of hydroxyethylmetacrylate and hydroxypropylmetacrylamide, copolymer of acrylamide, butylacrylate, maleinanhydride, and methylmetacrylate, and the like], or else cationised natural polysaccharides such as starches, celluloses, or gums such as guargumhydroxypropyltriammonium chloride.
   b) Synthetic or semi-synthetic polyaminoacids such as polylysin, polyarginin, α,β-poly-[N-(2-hydroxyethyl)-DL-asparamide. Synthetic antifibrinolytics hexadimethrindibromide (polybren) can also be included in this group.
2. Natural or semi-synthetic peptides such as gelatine, protamines, or fibrinopeptides, and their derivatives.
3. Natural aminoglucanes such as fractionated chitin and its de-acetylated derivative chitosan, of microbial origin or isolated from the shells of arthropods such as crabs.

In preparing IMCs on the basis of PAGA according to the invention these three groups of substances can be combined to obtain required properties of the final product.

In general it can be said that IMCs using substances from 1a and 1b would preferably be used to prepare various types of highly absorbant biocompatible dressing materials in the form of nonwovens, films, plasters, and pads.

IMCs using the substances from 2 and 3 may serve as efficient haemostatic agents for internal applications in the microfibrillar form, in the microdispersed form as dusting powders, in the form of films, granules, tablets or nonwoven textile-like structures. Those preparations also display antiadhesive properties.

We have also found out that in the form of film-like cell culture matrices the latter IMCs incorporating PAGA and salts thereof as prepared according to PCT IE 98/00004 have a favourable effect on the growth of fibroblasts and keratinocytes.

While it is also possible to create IMCs using structural scleroproteins of the collagen type as disclosed in WO 9800180A, it is preferable to use the above mentioned groups of substances because of the possibility of contamination of the final product by telopeptides, viruses or pyrogens. Collagen can affect in an uncontrolled manner, the immune response of the organism because formation of antibodies can be provoked by any portion of the collagen structure even though the main determinants occur in the terminal regions of the collagen macromolecule. Removal of telopeptides only partially solves the antigenicity problem (Michaeli et al: Science, 1969, 166, 1522).

By preparing IMCs according to the invention it is possible to essentially enhance properties of the originally prepared glucoronoglucanes such as 1,4 β PAGA. For instance an intermolecular complex salt of PAGA and gelatine in one single production step can be used to prepare final products in the form of a non woven, film, microdispersed granules, or dispersions. In contrast to collagen, suitably hydrolysed gelatine is well tolerated, has no toxicity or side effects and it is a much less costly raw material. We have found out that this complex has very good haemostatic properties being about 40% higher than the original PAGA calcium sodium salt. This is despite the fact that the gelatine itself only displays a haemostatic effect after an addition of thrombin [Schwartz S. I. et al.: Principles of Surgery, St. Louis: McGraw Hill Co, 1979, p. 122–123]. In this case the absorption in the organism can be controlled by changing the composition of the complex within the range from tens of hours to several months. This complex has a higher haemostatic efficiency and can be used as an embolisation or microembolisation product. It can also be used to prepare haemostatic layers of highly absorbent multi-layer dressings or resorbable plasters, though more costly polybren or protamines could also be applied.

An important advantage of these IMCs is the fact that the compounds can be prepared within a single manufacturing operation using the hydrolytic process described in PCT IE 98/00004 which makes these products cost effective.

These IMCs can further be modified by biologically active and/or biologically acceptable substances. Because the IMCs prepared by the present procedure are either of a microdispersed or microfibrillar nature, the active substances tend to be bound uniformly and also are uniformly released in the organism without the need for other adjuvants such as microcrystalline waxes or stearates. However, the addition of such adjuvants is not excluded.

Biologically active substances which can be incorporated into the IMC may involve, for instance, antibiotics carrying at least a weak positive charge in the molecule such as cephalosporins (cephotaxin), aminoglycosides (neomycin, gentamycin, amikacin), penicillins (tikarcilin) or macrolides (erythromycin, clarithromycin) and the like.

In cases where the calcium/sodium salt of PAGA or its IMC complexes according to the invention are used as microembolisation or embolisation agents in regional chemotherapy of malign tumours, suitable types of cytostatics such as adriamycin or derivatives of 1,4-diaminoanthrachinone can be incorporated. It is also possible to use the IMCs as detaching ligands for platinum(II) based cytostatics.

Biologically acceptable substances used for modification of the IMCs include, for instance, glycerol and its polymers polyglycerols); mono, di, and certain triglycerides: polyethyleneglycols; monopropyleneglycol; block copolymers of polyethyleneoxides and polypropyleneoxides (Pluronic); starches; cyclodextines; polyvinylalcohols; cellulose and its derivatives; in general, substances that, in the concentrations used, are not irritating or toxic for the living organism while being capable of further optimising the physicomechanical properties of the final product based on the IMCs according to the invention.

The invention will be more clearly understood from the following examples of polymer complexes of glucuronoglucanes.

EXAMPLE 1

Material long-fibre cotton—medicinal cotton wool oxidised by $N_xO_y$ (proprietary)

| | |
|---|---|
| $C_6$OOH | 18.8% b/w |
| ash content | <0.1% b/w |
| Σ C=O | 0.6% b/w |

20% solution $Na_2CO_3$ (Lachema, a.s. Neratovice)
$CaCl_2.6H_2O$ anal.grade (Lachema, a.s. Neratovice)
demineralised water 2 μS
ethanol, synthetic rectified conc. 98% (Chemopetrol Litvínov, a.s.)
acid acetic anal.grade (Lachema, a.s. Neratovice)
$H_2O_2$ anal.grade 30% (Lachema, a.s. Neratovice)
N-HANCE 3000 guargumhydroxypropyltriammoniumchloride
(Aqualon-Hercules)

Equipment mixer: bottom stirring, 150 litre (duplicator), stainless steel EXTRA
vibrating screen: stainless steel, 150 mesh
rotary air pump: rotor diameter 150 mm
turbostirrer: ULTRA TURAX (Janke-Kunkel)
beaker: 5 litre
pH meter PICCOLO
thermocouple thermometer Procedure 30 g of N-HANCE 3000 were placed into a 5 l beaker and 3 l of demineralised water 2 μS were added. The contents of the beaker were intensely stirred for 30 minutes. The pH value was adjusted to less than 4.5 by the addition of an acetic acid solution leading to a viscosity rise.

60 l of demineralised water 2 μS were introduced into a mixer. 3 kg of $CaCl_2.6H_2O$ anal.grade were added and the contents heated up to a temperature of 50° C. with stirring. On dissolution of the calcium chloride the stirring was interrupted and 2.7 kg of the raw oxidised cotton wool were introduced. The mixer was closed and the contents were agitated for 120 seconds. The pH value of the contents was adjusted by addition of a 20% solution of $Na_2CO_3$ to 6–6.5 and 13 kg of $H_2O_2$ 30% were introduced. The fibre suspension was slowly agitated for 10 minutes. Then the pH value was readjusted to 4.5–5.0 and the prepared viscous solution of N-HANCE 3000 was introduced. The contents of the mixer were stirred intensely for 30 seconds. Subsequently 60 l of synthetic rectified ethanol conc. 98% were introduced into the mixer. 15 seconds after adding the ethanol the contents of the mixer were transferred onto a vibrating screen, and the supernatant liquid was filtered off. The filtration cake was redispersed in the mixer in 60 l of a mixture of 18 l of synthetic rectified ethanol conc. 98% and 42 l of demineralised water 2 μS. The fibre suspension was filtered again on the vibrating screen.

The isolated material thus prepared may further serve to prepare final products of the nonwoven type via a wet or dry process.

Analysis

| | |
|---|---|
| Ca content | 4.0% b/w |
| Na content | 1.8% b/w |
| Σ C=O content | 0.0% b/w |
| COOH content | 20.7% b/w |

EXAMPLE 2

Material oxidised short-fibre cotton (Linters-Temming) (proprietary)

| | |
|---|---|
| $C_6$OOH | 16.8% b/w |
| ash content | <0.15% b/w |
| Σ C=O | 2.6% b/w |

20% solution $Na_2CO_3$ (Lachema, a.s. Neratovice)
$CaCl_2.6H_2O$ anal.grade (Lachema, a.s. Neratovice)
redistilled water (PhBs 1997)
ethanol, synthetic rectified conc. 98% (Chemopetrol Litvínov, a.s.)
isopropanol 99.9% (Neuberg Bretang)
$H_2O_2$ anal.grade 30% (Lachema, a.s. Neratovice)
gelatine (PhBs 1997)

Equipment
- turbostirrer: ULTRA TURAX (Janke-Kunkel)
- sulphonation flask 1 litre
- heater 1.5 kW
- laboratory centrifuge: 4000 rpm
- thermostated water bath
- pH meter PICCOLO
- glass thermometer
- rotary vacuum dryer or hot-air dryer Procedure Into a 1 litre sulphonation flask equipped with a turbostirrer and a heater, 400 ml of redistilled $H_2O$ were placed, 15.73 g of $CaCl_2.6H_2O$ were added and on dissolution, 40.0 g of 20% $Na_2CO_3$ solution were introduced under stirring. Subsequently, 50 g of oxidised Linters were added to the white emulsion formed and the contents were heated up to 95° C. with the stirring intensity set to a maximum. After 10 minutes, 30 g of 30% $H_2O_2$ were added into the flask and the hydrolysis continued for another 10 minutes. The contents were then cooled down to 60° C. on a water bath and the pH of the system was adjusted to a value of 4.5–5.0 by the addition of a 20% solution of $Na_2CO_3$. A gelatine solution (10 g of gelatine in 70 g of redistilled $H_2O$) warmed to 50° C. was added and left to react for another 20 minutes. The flask contents were then cooled to 30° C. in a water bath and 626 ml of synthetic rectified ethanol conc. 98% were added gradually under intense stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and allowed stand for 4 hours. It was then centrifuged again, redispersed into 99.9% isopropanol, and left to stand for a minimum of 10 hours at 20° C. The gel formed was centrifuged and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

Analysis

| | |
|---|---|
| content Ca | 4.4% b/w |
| content Na | 2.7% b/w |
| content Σ C=O | 0.0% b/w |
| content COOH | 20.5% b/w |
| content N | 1.8% b/w |

EXAMPLE 3

Material
- oxidised short-fibre cotton (Linters-Temming) (proprietary)

| | |
|---|---|
| $C_6OOH$ | 16.8% b/w |
| ash content | <0.15% b/w |
| Σ C=O | 2.6% b/w |

- NaOH anal.grade (Lachema, a.s. Neratovice)
- redistilled water (PhBs 1997)
- ethanol, synthetic rectified conc. 98% (Chemopetrol Litvínov, a.s.)
- isopropanol 99.9% (Neuberg Bretang)
- $H_2O_2$ anal.grade 30% (Lachema, a.s. Neratovice)
- gelatine (PhBs 1997)

Equipment
- turbostirrer ULTRA TURAX (Janke-Kunkel)
- sulphonation flask 1 litre
- heater 1.5 kW
- laboratory centrifuge: 4000 rpm
- thermostated water bath
- pH meter PICCOLO
- glass thermometer
- rotary vacuum dryer or hot-air dryer Procedure Into a 1 litre sulphonation flask equipped with a turbostirrer and a heater, 400 ml of redistilled $H_2O$ were placed, and 8 g of NaOH were added. On dissolution, 50 g of oxidised Linters were added, the contents were heated up to 70° C. and the stirring intensity set to a maximum. After 20 minutes, 40 g of 30% $H_2O_2$ were added into the flask, the temperature was increased to 85° C., and maintained for another 10 minutes. The contents were then cooled to 50° C. on a water bath and gelatine solution (10 g of gelatine in 70 g of redistilled $H_2O$) warmed 50° C. was added to the hydrolysate. The temperature was decreased to 25–30° C. and the pH of the system was checked and adjusted to a value of 6.0–6.5. Subsequently, 626 ml of synthetic rectified ethanol conc. 98% were added gradually under intense stirring. The suspension of IMC thus formed was isolated using a laboratory centrifuge. The supernatant liquid was filtered away and the cake was redispersed into 250 ml of 50% ethanol. The system was centrifuged and after the separation of the supernatant liquid, the IMC was redispersed into 250 ml of synthetic rectified ethanol conc. 98% and left to stand for 4 hours. It was then centrifuged, redispersed into 99.9% isopropanol, and allowed stand for a minimum of 10 hours at 20° C. The gel formed was centrifuged and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

Analysis

| | |
|---|---|
| Na content | 3.8% b/w |
| Σ C=O content | 0.0% b/w |
| COOH content | 21.5% b/w |
| N content | 2.7% b/w |

EXAMPLE 4

Material
- oxidised short-fibre cotton (Linters-Temming) (proprietary)

| | |
|---|---|
| $C_6OOH$ | 16.8% b/w |
| ash content | <0.15% b/w |
| Σ C=O | 2.6% b/w |

- 20% solution $Na_2CO_3$ (Lachema, a.s. Neratovice)
- $CaCl_2.6H_2O$ anal.grade (Lachema, a.s. Neratovice)

redistilled water (PhBs 1997)
ethanol, synthetic rectified conc. 98% (Chemopetrol Litvínov, a.s.)
isopropanol 99.9% (Neuberg Bretang)
$H_2O_2$ anal.grade 30% (Lachema, a.s. Neratovice)
chitosan, degree of deacetylation 92% (Henkel)

Equipment turbostirrer: ULTRA TURAX (Janke-Kunkel)
sulphonation flask 1 litre
heater 1.5 kW
laboratory centrifuge: 4000 rpm
thermostated water bath
pH meter PICCOLO
glass thermometer
rotary vacuum dryer or hot-air dryer Procedure Into a sulphonation flask, 250 ml redistilled $H_2O$ were placed, and 5 g of NaOH were added. On dissolution, 25 g of oxidised Linters were introduced under stirring, the temperature increased to 50° C. and the stirring intensity set to a maximum. After hydrolysing for 15 minutes, 35 g of 30% $H_2O_2$ were gradually added to the system and the temperature was maintained at 50° C. for another 20 minutes. The contents were cooled to 30° C. and 400 g of highly viscous 5% solution of chitosan were added. The flask contents were then intensely stirred for another 10 minutes, and the pH of the system was adjusted by the addition of NaOH to a value of 7.0. Subsequently 300 ml of synthetic rectified ethanol conc. 98% were added with stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and left to stand for 4 hours. It was then centrifuged again, redispersed into 99.9% isopropanol, and left for a minimum of 10 hours at 20° C. The gel formed was centrifuged and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

Analysis

| | |
|---|---|
| Na content | 1.8% b/w |
| $\Sigma$ C=O content | 0.0% b/w |
| COOH content | 10.4% b/w |
| N content | 28% b/w |

EXAMPLE 5

Material oxidised short-fibre cotton (Linters-Temming) (proprietary)

| | |
|---|---|
| $C_6OOH$ | 16.8% b/w |
| ash content | <0.15% b/w |
| $\Sigma$ C=O | 2.6% b/w |

NaOH anal.grade (Lachema, a.s. Neratovice)
HCl 39% anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)
Ambroxol (H. Mack, Germany)

Equipment turbostirrer: ULTRA TURAX (Janke-Kunkel)
sulphonation flask 2 l
heater 1.5 kW
laboratory centrifuge: 4000 rpm
laboratory pin mill ALPINE (35 000 rpm)
thermostated water bath
pH meter PICCOLO
glass thermometer
rotary vacuum dryer or hot-air dryer Procedure Into a sulphonation flask, 400 ml redistilled $H_2O$ were placed, and 8 g of NaOH were added. On dissolution, 50 g of oxidised Linters were introduced under stirring, the temperature increased to 70° C. and the stirring intensity was set to a maximum. After hydrolysing for 20 minutes, 40 g of 30% $H_2O_2$ were gradually added to the system and the temperature was increased to, and maintained at, 85° C. for another 10 minutes. The content were cooled down to 50° C. in a water bath, and gelatine solution (2 g of gelatine in 70 g of redistilled $H_2O$) warmed up to 50° C. was added to the hydrolysate. The temperature was decreased to 25–30° C. and the pH of the system was checked and adjusted to a value of 1.6–1.8 by addition of 39% HCl. Under intense stirring, a solution of Ambroxol (25 g of ambroxolium hydrochloride in 500 ml of redistilled $H_2O$) was added gradually. After agitating for 5 minutes the pH value was adjusted to 4.3–4.6 by adding 5% NaOH solution, and 626 ml of synthetic rectified ethanol conc. 98% were added under intense stirring. The suspension of Ambroxol containing IMC thus formed was isolated using a laboratory centrifuge. The supernatant liquid was filtered away and the cake was redispersed into, subsequently, 800 ml of 60% ethanol and 250 ml of 98% ethanol, wherein it was let to stay for a minimum of 10 hours. The system was centrifuged again and the product was dried at 40° C. in a rotary vacuum dryer or a hot-air dryer. A white to slightly yellowish powder was obtained and further desagglomerated on an Alpine pin mill.

The product serves for the preparation of a mucoregulatory drug with a prolonged action.

Analysis

| | |
|---|---|
| Na content | 4.6% b/w |
| $\Sigma$ C=O content | 0.0% b/w |
| COOH content | 14.8% b/w |
| N content | 1.9% b/w |

EXAMPLE 6

Material
  oxidised short-fibre cotton (Linters-Temming) (proprietary)

| | |
|---|---|
| C$_6$OOH | 16.8% b/w |
| ash content | <0.15% b/w |
| Σ C=O | 2.6% b/w |

20% solution Na$_2$CO$_3$ (Lachema, a.s. Neratovice)
CaCl$_2$.6H$_2$O anal.grade (Lachema, a.s. Neratovice)
redistilled water (PhBs 1997)
ethanol, synthetic rectified conc. 98% (Chemopetrol Litvínov, a.s.)
isopropanol 99.9% (Neuberg Bretang)
H$_2$O$_2$ anal.grade 30% (Lachema, a.s. Neratovice)
gelatine (PhBs 1997)
gentamycin sulphate (MERCK)

Equipment
  turbostirrer: ULTRA TURAX (Janke-Kunkel)
  sulphonation flask 2 litre
  heater 1.5 kW
  laboratory centrifuge: 4000 rpm
  laboratory pin mill ALPINE (35 000 rpm)
  thermostated water bath
  pH meter PICCOLO
  glass thermometer
  hot-air dryer
  lyophiliser (Leibold Heraus, Germany)

Procedure

Into a 2 litre sulphonation flask equipped with a turbostirrer and a heater, 400 ml of redistilled H$_2$O were placed, 15.73 g of CaCl$_2$.6H$_2$O were added and on dissolution, 40.0 g of 20% Na$_2$CO$_3$ solution were introduced under stirring. Subsequently, 50 g of oxidised Linters were added to the white emulsion formed and the contents were heated up to 95° C. and the stirring intensity set to a maximum. After 10 minutes, 30 g of 30% H$_2$O$_2$ were added into the flask and the hydrolysis was continued for another 10 minutes. The contents were then cooled down to 60° C. on a water bath and the pH of the system was adjusted to a value of 4.5–5.0 by addition of 20% solution of Na$_2$CO$_3$. A gelatine solution (10 g of gelatine in 70 g of redistilled H$_2$O) warmed up to 50° C. was added and let to react for another 20 minutes. The flask contents were then cooled down to 30° C. in a water bath and 40 g of gentamycin sulphate in 600 ml of redistilled H$_2$O were added gradually within 10 minutes. 626 ml of synthetic rectified ethanol conc. 98% were then added gradually with intense stirring to the antibiotic containing IMC suspension formed. The suspension of IMC thus formed was isolated using a laboratory centrifuge. The supernatant liquid was filtered away and the cake was redispersed into 250 ml of 50% ethanol. The system was centrifuged and after the separation of the supernatant liquid, the IMC was redispersed into 250 ml of synthetic rectified ethanol conc. 98% and left for 4 hours. It was then centrifuged, redispersed into 99.9% isopropanol, and left for a minimum of 10 hours at 20° C. The gel formed was centrifuged and the product was dried in a rotary vacuum dryer or a hot-air dryer.

The product can be used, for instance, for the manufacture of a dusting powder or a powder spray for the treatment of infected wounds.

Analysis

| | |
|---|---|
| Ca content | 2.4% b/w |
| Na content | 1.6% b/w |
| Σ C=O content | 0.0% b/w |
| COOH content | 9.6% b/w |
| N content | 2.7% b/w |

EXAMPLE 7

Material
  long-fibre cotton-medicinal cotton wool oxidised by N$_x$O$_y$ (proprietary)

| | |
|---|---|
| C$_6$OOH | 18.8% b/w |
| ash content | <0.1% b/w |
| Σ C=O | 0.6% b/w |

20% solution Na$_2$CO$_3$ (Lachema, a.s. Neratovice)
CaCl$_2$.6H$_2$O anal.grade (Lachema, a.s. Neratovice)
demineralised water 2 μS
ethanol, synthetic rectified conc. 98% (Chemopetrol Litvínov, a.s.)
isopropanol 99.9% (Neuberg Bretang)
acid acetic anal.grade (Lachema, a.s. Neratovice)
H$_2$O$_2$ anal.grade 30% (Lachema, a.s. Neratovice)
N-HANCE 3000 guargumhydroxypropyltriammoniumchloride (Aqualon-Hercules)
polybren (hexadimethrindibromide) (FLUKA)
chlorhexidindigluconate Equipment
  mixer: bottom stirring, 150 l (duplicator), stainless steel EXTRA S
  vibrating screen: stainless steel, 150 mesh
  rotary air pump: rotor diameter 150 mm
  turbostirrer: ULTRA TURAX (Janke-Kunkel)
  beaker: 5 litre
  pH meter PICCOLO
  thermocouple thermometer Procedure 30 g of N-HANCE 3000 were placed into and 5 l beaker and 3 l of demineralised water 2 μS were added. Contents of the beaker were stirred intensely for 30 minutes. The pH value was adjusted to less than 4.5 by the addition of an acetic acid solution leading to a viscosity rise.

60 l of demineralised water 2 μS were introduced into a mixer. Then 3 kg of CaCl$_2$.6H$_2$O anal.grade were added and the contents heated up to a temperature of 50° C. under stirring. On dissolution of the calcium chloride the stirring was interrupted and 2.7 kg of the raw oxidised cotton wool were introduced. The mixer was closed and the contents were agitated for 120 seconds. Then the pH value of the contents was adjusted by the addition of a 20% solution of Na$_2$CO$_3$ to 6–6.5 and 13 kg of H$_2$O$_2$ 30% were introduced. The fibre suspension was slowly agitated for 10 minutes. The pH value was readjusted to 4.5–5.0 and the prepared viscous solution of N-HANCE 3000 was introduced. The contents of the mixer were stirred intensely for 30 seconds. A solution of 35 g of chlorhexidine digluconate in 350 ml of demineralised water 2 μS was then introduced slowly within 10 minutes. Within another 10 minutes, a solution of polybren containing 120 g of polybren in 1000 ml of demineralised water 2 µS was added. Subsequently 60 l of synthetic rectified ethanol conc. 98% were introduced into the mixer. 15 seconds after adding the ethanol, the contents of the mixer were transferred onto a vibrating screen, and the supernatant liquid was filtered off. The filtration cake was redispersed in the mixer in 60 l of a mixture of 18 l of synthetic rectified ethanol conc. 98% and 42 l of demineralised water 2 µS. The fibre suspension was filtered again on the vibrating screen.

The isolated material thus prepared may further serve to prepare, via a wet or dry process, final products of the non-woven type having an enhanced haemostatic activity and a bactericidal effect.

Analysis

| | |
|---|---|
| Ca content | 3.6% b/w |
| Na content | 1.9% b/w |
| Σ C=O content | 0.0% b/w |
| COOH content | 18.1% b/w |
| N content | 0.35% b/w |

EXAMPLE 8

Material
  oxidised short-fibre cotton (Linters-Temming) (proprietary)

| | |
|---|---|
| $C_6$OOH | 16.8% b/w |
| ash content | <0.15% b/w |
| Σ C=O | 2.6% b/w |

20% solution $Na_2CO_3$ (Lachema, a.s. Neratovice)
  $CaCl_2.6H_2O$ anal.grade (Lachema, a.s. Neratovice)
  redistilled water (PhBs 1997)
  ethanol, synthetic rectified conc. 98% (Chemopetrol Litvinov, a.s.)
  isopropanol 99.9% (Neuberg Bretang)
  $H_2O_2$ anal.grade 30% (Lachema, a.s. Neratovice)
  Chitosan, degree of deacetylation 92% (Henkel)
  Clarithromycin lactobionan (Abbott Laboratories, Italy)

Equipment
  turbostirrer: ULTRA TURAX (Janke-Kunkel)
  sulphonation flask 1 litre
  heater 1.5 kW
  laboratory centrifuge: 4000 rpm
  thermostated water bath
  pH meter PICCOLO
  glass thermometer
  rotary vacuum dryer or hot-air dryer
  dialysing bag (regenerated cellulose)
  lyophiliser (Leybold Heraus, Germany)
  laboratory pin mill ALPINE (35 000 rpm)

Procedure
  Into a sulphonation flask 250 ml redistilled $H_2O$ were placed and 5 g of NaOH were added. On dissolution, 25 g of oxidised Linters were introduced under stirring, the temperature increased to 50° C. and the stirring intensity set to a maximum. After hydrolysing for 15 minutes, 35 g of 30% $H_2O_2$ were gradually added to the system and the temperature was maintained at 50° C. for another 20 minutes. The content were cooled down to 30° C. and 400 g of highly viscous 2% solution of chitosan, having a pH value of 3.5, were added. The flask contents were then intensely stirred for another 10 minutes, and the pH of the system was adjusted, by addition of NaOH, to a value of 7.0. During another 10 minutes, a solution of clarithromycin (44 g of clarithromycin in 456 ml of redistilled $H_2O$) was introduced and the pH of the system was adjusted to a value of 7.0–7.5. Stirring was interrupted, the flask contents were transferred into a dialysing bag and dialysed against water for 48 hours. Subsequently the product was isolated by centrifugation, lyophilised, and disintegrated using the laboratory pin mill ALPINE.

The product can be used, for instance, to prepare tablets or granules efficient against Helicobacter pylori occurring in the gastrointestinal tract.

Analysis

| | |
|---|---|
| Na content | 4.8% b/w |
| Σ C=O content | 0.0% b/w |
| COOH content | 18.8% b/w |
| N content | 0.7% b/w |

EXAMPLE 9

Material
  oxidised short-fibre cotton (Linters-Temming) (proprietary)

| | |
|---|---|
| $C_6$OOH | 16.8% b/w |
| ash content | <0.15% b/w |
| Σ C=O | 2.6% b/w |

NaOH anal.grade (Lachema, a.s. Neratovice)
  redistilled water (PhBs 1997)
  ethanol, synthetic rectified conc. 98% (Chemopetrol Litvinov, a.s.)
  isopropanol 99.9% (Neuberg Bretang)
  $H_2O_2$ anal.grade 30% (Lachema, a.s. Neratovice)
  gelatine (PhBs 1997)
  $Bi(NO_3)_3.5H_2O$ (MERCK)

Equipment
  turbostirrer: ULTRA TURAX (Janke-Kunkel)
  sulphonation flask 2 litre
  heater 1.5 kW
  laboratory centrifuge: 4000 rpm
  thermostated water bath
  pH meter PICCOLO
  glass thermometer
  rotary vacuum dryer or hot-air dryer Procedure
  Into a sulphonation flask 400 ml redistilled $H_2O$ were placed and 8 g of NaOH were added. On dissolution, 50 g of oxidised Linters were introduced under stirring, the temperature increased to 70° C. and the stirring intensity was set to a maximum. After hydrolysing for 20 minutes, 40 g of 30% $H_2O_2$ were gradually added to the system and the temperature was increased to, and maintained at, 85° C. for another 10 minutes. The contents were cooled down to 50° C. in a water bath, and a gelatine solution (0.5 g of gelatine in 50 ml of redistilled $H_2O$) warmed up to 50° C. was added to the hydrolysate. The temperature was decreased to 25–30° C. and the pH of the system was checked and adjusted to a value of 1.6–1.8 by addition of 39% HCl. A freshly prepared solution of $BiNO_3$ (54 g of $BiNO_3.5H_2O$ in 746 ml of $H_2O$) was introduced and the temperature maintained for another 15 minutes. The temperature was decreased to 25–30° C. and the pH of the system was checked and readjusted to a value of 5.5–6.0. 626 ml of synthetic rectified ethanol conc. 98% were then added gradually with intense stirring. The $BiO^+$ containing IMC suspension thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and left for a minimum of 4 hours. It was then centrifuged again, redispersed into 99.9% isopropanol, and left for a minimum of 10 hours at 20° C. The suspension formed was then centrifuged again and the product was dried in a rotary vacuum dryer or a hot-air dryer.

The product can be used, for instance, to prepare dusting powders for wound treatment or tablets for treatment of gastrointestinal tract malfunctions.

Analysis

| | |
|---|---|
| Na content | 1.9% b/w |
| Σ C=O content | 0.0% b/w |
| COOH content | 20.0% b/w |
| N content | <0.3% b/w |
| Bi content | 4.7% b/w |

EXAMPLE 10

Material oxidised short-fibre cotton (Linters-Temming) (proprietary)

| | |
|---|---|
| $C_6OOH$ | 16.8% b/w |
| ash content | <0.15% b/w |
| Σ C=O | 2.6% b/w |

20% solution $Na_2CO_3$ (Lachema, a.s. Neratovice)
   $CaCl_2.6H_2O$ anal.grade (Lachema, a.s. Neratovice)
   redistilled water (PhBs 1997)
   ethanol, synthetic rectified conc. 98% (Chemopetrol Litvínov, a.s.)
   isopropanol 99.9% (Neuberg Bretang)
   $H_2O_2$ anal.grade 30% (Lachema, a.s. Neratovice)
   gelatine (PhBs 1997)
   cimetidine hydrochloride (SPOFA)

Equipment
   turbostirrer: ULTRA TURAX (Janke-Kunkel)
   sulphonation flask 2 litre
   heater 1.5 kW
   laboratory centrifuge: 4000 rpm
   thermostated water bath
   pH meter PICCOLO
   glass thermometer
   rotary vacuum dryer or hot-air dryer Procedure Into a 1 l sulphonation flask equipped with a turbostirrer and a heater, 400 ml of redistilled $H_2O$ were placed. 15.73 g of $CaCl_2.6H_2O$ were added and on dissolution 40.0 g of 20% $Na_2CO_3$ solution were introduced with stirring. 50 g of oxidised Linters were added to the white emulsion formed and the contents were heated up to 95° C. and the stirring intensity set to a maximum. After 10 minutes, 30 g of 30% $H_2O_2$ were added into the flask and the hydrolysis was continued for another 10 minutes. The contents were then cooled down to 60° C. on a water bath and the pH of the system was adjusted to a value of 4.5–5.0 by addition of 20% solution of $Na_2CO_3$. A gelatine solution (10 g of gelatine in 70 g of redistilled $H_2O$) warmed up to 50° C. was added and allowed react for another 20 minutes. The flask contents were then cooled down to 30° C. in a water bath and a solution of cimetidine (36 g of cimetidine hydrochloride in 400 ml of redistilled $H_2O$) were added with intense stirring. The contents were intensely agitated for 10 minutes and 800 ml of synthetic rectified ethanol conc. 98% were added gradually. The suspension of IMC thus formed was isolated using a laboratory centrifuge. The supernatant liquid was filtered away and the cake was redispersed into 250 ml of 50% ethanol. The system was centrifuged and after separation of the supernatant liquid, the IMC was redispersed into 250 ml of synthetic rectified ethanol conc. 98% and left for 4 hours. It was then centrifuged again, redispersed into 99.9% isopropanol, and left for a minimum of 10 hours at 20° C. The gel formed was centrifuged again and the product was dried in a rotary vacuum dryer or a hot-air dryer.

The product can be used, for instance, to manufacture tablets or granulates for the treatment of the gastrointestinal tract or other non-malignant ulcerations.

Analysis

| | |
|---|---|
| Ca content | 4.4% b/w |
| Na content | 2.7% b/w |
| Σ C=O content | 0.0% b/w |
| COOH content | 20.5% b/w |
| N content | 2.1% b/w |

EXAMPLE 11

Material
   IMC-microdispersed oxidised cellulose (MDOC) complex (as per above Example 2)
   [(2S;2R)-3-amino-2-hydroxy-4-phenylbutenoyl]-L-leucin (Bestatin)
   (Boehringer Mannheim, Germany)
   redistilled water (PhBs 1997)
   methanol, conc. anal.grade (Chemopetrol Litvínov, a.s.)
   diethylether (Lachema, a.s. Neratovice)

Equipment
   turbostirrer: ULTRA TURAX (Janke-Kunkel)
   sulphonation flask 2 l
   laboratory centrifuge: 4000 rpm
   hot-air dryer Procedure The IMC-MDOC complex as prepared in Example 2 above was redispersed into redistilled water in a sulphonation flask using a turbostirrer. A solution of Bestatin in methanol was added to the flask in an amount sufficient to yield a 10% b/w concentration of Bestatin in the resulting Bestatin-gelatine-MDOC complex. After thorough homogenisation, the suspension formed was isolated by centrifugation. The supernatant liquid was filtered away and the filtration cake was redispersed into concentrated methanol, centrifuged, redispersed in diethylether, and after being left for 1 hour, it was dried in a hot-air dryer.

The product, a microdispersed form of a Bestatin-gelatine-MDOC complex, can be used, for instance, to prepare microembolisation agents used in regional chemotherapy of malignant tumours or flat dressing structures for wound treatment.

The following are application examples illustrating some of the uses of the products produced in examples 1 to 11.

EXAMPLE A

Preparation of Tablets and Pellets from IMC-MDOC Complex

MDOC=Microdispersed Oxidised Cellulose
Material
  IMC-MDOC complex—see Example 2
  magnesium stearate (SIGMA)
  ascorbic acid (MERCK)
  α-tocoferol acetate (Slovakofarma Hlohovec)
  ethanol synthetic rectified (Chemopetrol Litvínov, a.s.)
Equipment
  tabletting machine (KORSCH EK 0, Berlin)
  blender (Nautamix 300)
  counter-flow drier BINDER
Procedure 10 kg of IMC-MDOC complex of composition according to Example 2 were placed into the blender, and 660 g of micronised ascorbic acid, 1660 g of α-tocoferol acetate emulgated in 2500 ml of ethanol, and 1000 g of magnesium stearate were added. The mixture was homogenised for 3 hours. It was then dried in a counter-flow drier at a temperature of 50° C. until ethanol was removed.

100 g of the resulting dry powder were introduced into the tabletting machine, and the tabletting force was set at a value of 7 kN.
Result The tablets prepared were smooth and well cohering and had a weight of 0.5 g. Disintegration rate of the tablets in a saline F1/1 was 17 minutes at 20° C., and 8 minutes at 37° C.

Application Example

Patient aged 57, displaying an increased cholesterol content in blood was treated by MDOC tablets administered orally for 50 days, at a dose of 6 tablets daily. After the treatment both LDL content and total cholesterol content were significantly reduced.

| Blood analysis: | before treatment | after treatment |
|---|---|---|
| Total Cholesterol | 7.70 mmol/l | 5.70 mmol/l |
| HDL | 1.16 mmol/l | 1.30 mmol/l |
| LDL | 4.40 mmol/l | 3.30 mmol/l |
| Triacylglycerols | 1.81 mmol/l | 1.80 mmol/l |

EXAMPLE B

Preparation of Tablets and Pellets with IMC-MDOC Complex Containing Clarithromycin
Material
  IMC-MDOC complex—see Example 8
  MDOC, particle size 0.1–2.0 μm, specific surface area 86 m², COOH group content 22.2% b/w, Ca content 4.2% b/w, Na content 3.8% b/w
  IMC-MDOC complex containing BiO$^+$—see Example 9
Equipment
  laboratory mixer, bottom agitated, 4000 rpm
  tabletting machine (KORSCH EK 0, Berlin)
Procedure 9.5 g of IMC-MDOC containing clarithromycin were placed into the mixer, and 12.0 g of BiO$^{30}$ salt and 78.5 g of MDOC were added. The vessel was closed, the agitation set on, and the contents were homogenised for 60 seconds. The homogenised mixture was then transferred to the storage vessel of the tabletting machine, and the tabletting force was set to a value of 7.5 kN.
Result The tablets prepared were smooth and cohering and had a weight of 0.5 g. Disintegration rate of the tablets in a saline F1/1 was 12 minutes at 20° C., and 5 minutes at 37° C.
Indication The tablets are indicated for treatment of gastric ulcers. MDOC suppresses formation of the stomach acidity, adjust the pH value of the environment, and protects the mucous membranes by forming a gel layer. BiO$^+$ acts as a mild astringens. Clarithromycin depresses the growth of Helicobacter pylori beyond pathologic limits.

EXAMPLE C

Preparation of Tablets and Pellets with IMC-MDOC Complex Containing Ambroxol
Material
  MDOC, particle size 0.1–2.0 μm, specific surface area 86 m², COOH group content 22.2% b/w, Ca content 4.2% b/w, Na content 3.8% b/w
  IMC-MDOC complex containing Ambroxol—see Example 5
  microcrystalline cellulose (SIGMA)
  hydroxypropylcellulose (Natrosol HHR 250)
  magnesium stearate (SIGMA)
  Macrogol 400 (SIGMA)
Equipment
  laboratory mixer, bottom agitated, 4000 rpm
  tabletting machine (KORSCH EK 0, Berlin)
Procedure 43.0 g of MDOC, 42.0 g of IMC-MDOC containing ambroxol, 10.0 g of microcrystalline cellulose, 2.0 g of magnesium stearate, 1.0 g of Macrogolu 400, and 2.0 g of Natrosol HHR250 were introduced into the mixer. The vessel was closed, agitation (4000 rpm) started and the contents were homogenised for 120 seconds. The homogenised mixture was then transferred to the storage vessel of the tabletting machine and the tabletting force was set at a value of 5.0 kN.
Result The tablets prepared were smooth and cohering and had a weight of 0.5 g. Disintegration rate of the tablets in a saline F1/1 was 10 minutes at 20° C., and 6 minutes at 37° C.
Indication Acute and chronic respiratory diseases involving formation of dense mucus (acute bronchitis, bronchial asthma), ease of mucus dissolution in rhinofaryngitis. In testing on volunteers at a dosage rate of 3 tablets per day, ambroxol could still be detected in the urine at Day 8 after administration.

EXAMPLE D

Preparation of Tablets and Pellets with IMC-MDOC Complex Containing Cimetidine Material
  MDOC, particle size 0.1–2.0 μm, specific surface area 86 m², COOH group content 22.2% b/w, Ca content 4.2% b/w, Na content 3.8% b/w
  IMC-MDOC complex containing cimetidine—see Example 10
  Macrogol 400 (SIGMA)

Equipment
  laboratory mixer, bottom agitated, 4000 rpm
  tabletting machine (KORSCH EK 0, Berlin)

Procedure
  63.0 g of IMC-MDOC containing cimetidine, 32.0 g of MDOC and 5.0 g of Macrogolu 400 were introduced into the mixer. The vessel was closed, the agitation set on, and the contents were homogenised for 60 seconds. The homogenised mixture was then transferred to the storage vessel of the tabletting machine, and the tabletting force was set to a value of 7.5 kN.

Result
  The tablets prepared were smooth and well cohering and had a weight of 1.0 g. Disintegration rate of the tablets in a saline F1/1 was 8 minutes at 20° C., and 6 minutes at 37° C.

Indication
  The tablets are indicated for treatment of gastric ulcers. MDOC suppresses formation of the stomach acidity, adjust the pH value of the environment, and protects the mucous membranes by forming a gel layer. BiO⁺ acts as a mild astringens. Cimetidine suppresses both basal and simulated secretion of the stomach acid.

EXAMPLE E

Preparation of Rectal Suppositories from IMC-MDOC BiO⁺ Complex Containing Aminophenazon and Allobarbital Material
  Adeps neutralis (WERBA)
  Oleum cacao (WERBA)
  IMC-MDOC complex containing BiO⁺—see Example 9
  Aminophenazonum (SPOFA)
  Allobarbitalum (SPOFA)

Equipment
  stainless melting tank, agitated, volume 1000 ml, input power 600 W
  movable support carrying a shaped blister foil Procedure
  282.6 g of Adeps neutralis and 122.6 g of Oleum cacao were introduced into the melting tank. The contents were heated up to a temperature of 75° C. On melting, 16 g of Allobarbitalum, 117.3 g of Aminophenozonum and 61.33 g of IMC-MDOC complex containing BiO⁺ were gradually added under permanent agitation. After appropriate homogenisation, the mass was cast into a shaped blister foil serving, when cooled down, as the suppository packaging.

Result
  Suppository of 8 mm diameter, 20 mm length, conical shape, weight 2.25 g.

Indication
  Combined suppositories having antihaemorrhoidal and analgetic/antipyretic effects.

EXAMPLE F

Preparation of Vaginal Suppositories from IMC-MDOC Complex Containing Gelatine, Nitrofurantoin and Chlorohexidine Material
  IMC-MDOC complex—see Example 2
  gelatina animalis (SIGMA)
  1,2-monopropylenglykol (SIGMA)
  glycerol, medicinal (MERCK)
  nitrofurantoinum (SPOFA) broad spectrum anti-microbial and anti-inflammatory
  chlorohexidine digluconate (FEROSAN)—local bactericide
  redistilled $H_2O$ Equipment
  stainless melting tank, agitated, volume 1000 ml, input power 600 W
  movable support carrying a shaped blister foil Procedure
  78 g of redistilled $H_2O$, 240 g of medicinal glycerol, 30 g of 1,2-MPG were introduced into the melting tank and the mixture was heated up to a temperature of 75° C. On melting, 30 g of nitrofurantoinu and 30 g of chlorohexidine were gradually added under agitation, and the mixture was agitated for another 15 minutes. Subsequently, 102 g of gelatine animalis were introduced and, after appropriate homogenisation, 90 g of IMC-MDOC complex were added. The resulting mixture was agitated for another 15 minutes and then the mass was cast into a shaped blister foil serving, when cooled down, as the suppository packaging.

Result
  Suppository of 8 mm diameter, 17 mm length, cylindrical shape, weight 2.0 g.

Indication
  Vaginal suppositories for use in treatment of urinary tract infections due to both grampositive and gramnegative bacterias, displaying a prolonged effect. The IMC-MDOC present serves to protect the vaginal mucous tissue and to create a natural microenvironment similar to the action of lactic acid.

EXAMPLE G

Preparation of Dental Pins from IMC-MDOC Complex Containing Bactericidal Agent Material
  IMC-MDOC complex—see Example 2
  chlorohexidine digluconate (FEROSAN)
  ethanol synthetic rectified 98%

Equipment
  laboratory mixer 4000 rpm
  tabletting machine (KORSCH EK 0, Berlin)

Procedure
  100 g of IMC-MDOC complex prepared according to Example 2 were placed into the mixer and a solution of 1.6 g of chlorohexidine digluconate in 20 g of ethanol was added under stirring. The mixture was homogenised for 120 seconds, and then introduced into the tabletting machine equipped with a set of special shaped moulds, and the tabletting force was set at a value of 5 kN.

Result
  Dental pins of a cone frustrum shape, 15 mm in height and 7 mm in base diameter, with lateral grooves to facilitate grasping the pin with tweezers.

Indication

Treatment of massive postextractional bleeding with simultaneous administration of a bactericidal agent.

EXAMPLE H

Preparation of Dental Pins from IMC-MDOC Complex with Antimicrobial Agent

Material
- IMC-MDOC complex containing chitosan—see Example 4
- MDOC, particle size 0.1–2.0 μm, specific surface area 86 m$^2$/g, COOH group content 22.2% b/w, Ca content 4.2% b/w, Na content 3.8% b/w
- polyvinylpyrrolidone-iodine complex PVP-I micronised (ISP-USA)

Equipment
- laboratory mixer 4000 rpm
- tabletting machine (KORSCH EK 0, Berlin)

Procedure 50 g of IMC-MDOC complex, 49 g of MDOC and 1 g of PVP-I complex were placed into the mixer. The mixture was homogenised for 120 seconds, and then introduced into the tabletting machine equipped with a set of special shaped moulds, and the tabletting force was set at a value of 5 kN.

Result

Dental pins of a cone frustrum shape, 15 mm in height and 7 mm in base diameter, with lateral grooves to facilitate grasping the pin with tweezers.

Indication

Treatment of massive postextractional bleeding with simultaneous administration of an antimicrobial agent.

EXAMPLE I

Preparation of Granules from IMC-MDOC Complex Containing Clarithromycin

Material
- IMC-MDOC complex—see Example 8
- MDOC, particle size 0.1–2.0 μm, specific surface area 86 m$^2$/g,
- COOH group content 22.2% b/w, Ca content 4.2% b/w, Na content 3.8% b/w
- IMC-MDOC complex containing BiO$^+$—see Example 9
- ethanol synthetic rectified 98%
- redistilled H$_2$O Equipment
- set of vibrating screens with mesh size 100, 150, 200, 250, 350, 500 μm
- mixer, bottom agitated, vessel size 1000 ml, 8000 rpm, equipped
- with a nozzle for inlet of the granulation medium
- counter-flow drier BINDER Procedure 100 g of MDOC were placed into the mixer, the mixer was closed and the agitation switched on. A mist of 88% aqueous solution of ethanol was gradually injected into the mixer at a rate of 10 g/45 seconds. The granulate formed was transferred to the counter-flow drier and dried at a temperature of 45° C. until the humidity content was reduced below 6% b/w. The dried granules were sieve-screened using the set of vibrating screens. The individual fractions were packaged into glass vials in amounts of 0.5–2.0 g each as required. The preparation was sterilised by γ irradiation with a dose of 25 kGy.

Indication

The granules can be used in the treatment of gastric ulcers. MDOC suppresses formation of the stomach acidity, adjust the pH value of the environment, and protects the mucous membranes by forming a gel layer. BiO$^+$ acts as a mild astringens. Clarithromycin depresses the growth of Helicobacter pylori beyond pathologic limits.

EXAMPLE J

Preparation of Granules from IMC-MDOC Complex

Material
- IMC-MDOC complex—see Example 2

Equipment
- set of vibrating screens with mesh size 100, 150, 200, 250, 350, 500 μm
- mixer, bottom agitated, vessel size 1000 ml, 8000 rpm, equipped
- with a nozzle for inlet of the granulation medium
- counter-flow drier BINDER Procedure 100 g of MDOC were placed into the mixer, the mixer was closed and the agitation switched on. Saturated water vapour was gradually injected into the mixer at a rate of 10 g/45 seconds. The granulate formed was transferred to the counter-flow drier and dried at a temperature of 45° C. until the humidity content was reduced below 6% b/w. The dried granules were sieve-screened using the set of vibrating screens. The individual fractions were packaged into glass vials in amounts of 0.5–2.0 g each as required. The preparation was sterilised by γ irradiation with a dose of 25 kGy.

Indication

The product may be used as a) an embolisation agent, or b) an antilipemicum.

EXAMPLE K

Preparation of Granules from IMC-MDOC Complex Containing Antimicrobial Agent

Material
- IMC-MDOC complex—see Example 2
- polyvinylpyrrolidone-iodine PVP-I complex micronised (ISP-USA)
- 1,2-monopropyleneglycol (MERCK)
- redistilled H$_2$O
- ethanol synthetic rectified 98% (Chemopetrol Litvínov, a.s.)

Equipment
- set of vibrating screens with mesh size 100, 150, 200, 250, 350, 500 μm
- mixer, bottom agitated, vessel size 1000 ml, 8000 rpm, equipped
- with a nozzle for inlet of the granulation medium
- counter-flow drier BINDER Procedure 90 g of IMC-MDOC complex, 5 g of PVP-I complex and 5 g of 1,2-MPG were placed into the mixer, the mixer was closed and the agitation switched on. A mist of 88% aqueous solution of ethanol was gradually injected into the mixer at a rate of 10 g/50 seconds. The granulate formed was transferred to the counter-flow drier and dried at a temperature of 45° C. until the humidity content was reduced below 6% b/w. The dried granules were sieve-screened using the set of vibrating screens. The fraction below 100 μm was used to prepare a dusting powder. The higher fractions were packaged into glass vials in amounts of 0.5–2.0 g each as required.

Indication

Haemostatic preparation with antimicrobial and antiviral effect (powder spray, dusting powder).

EXAMPLE L

Preparation of Microspheres from IMC-MDOC Complex Containing Mitoxanthron

Material

IMC-MDOC complex—see Example 3

1,4-bis-2-(-2-hydroxyethylamino-ethylamino-)5,8-dihydroxyantrachinon (mitoxanthron) (Aliachem a.s.)

ethanol synthetic rectified 98% (Chemopetrol Litvínov, a.s.)

redistilled $H_2O$

Equipment turbostirrer ULTRA TURAX (Janke-Kunkel)

sulphonation flask 1 l beaker 250 ml set of vibrating screens with mesh size 100, 150, 200, 250, 350, 500 $\mu$m counter-flow drier BINDER vial 10 ml injection syringe 25 ml Procedure 80 g of redistilled water and 20 g of IMC-MDOC complex were introduced into the beaker, and the complex was dispersed using the turbostirrer to obtain a colloidal solution thereof.

495 ml of 98% ethanol was placed into the sulphonation flask. 1.0 g of mitoxanthron hydrochloride was placed into the 10 ml vial and dissolved in 5 g of redistilled water. The solution was then transferred into the sulphonation flask with ethanol under stirring.

The colloidal solution of IMC-MDOC complex was then gradually introduced into the mitoxanthron solution by being dropped, via the injection syringe, at a rate of 20 drops per minute into the sulphonation flask. The microspheres were isolated by filtration from the supernatant liquid, cautiously redispersed into 250 ml of 98% ethanol and allowed to stay for 4 hours. The ethanol was then removed by filtration and the microspheres were dried in the counter-flow drier at a temperature of 40° C. until the humidity content was reduced below 3% b/w. The dry microspheres containing 50 mg of mitoxanthron per 1 g were sieve-screened using the set of vibrating screens, and packaged into glass vials in amounts of 0.5 g each.

Indication

Intraarterial (regional) chemotherapy of malignant tumours where mitoxanthron is indicated.

EXAMPLE M

Preparation of Microspheres from IMC-MDOC Complex Containing Mitoxanthron

Material

MDOC (Ca/Na salt of PAGA), particle size 0.1–2.0 $\mu$m, specific surface area 86 $m^2$/g, COOH group content 22.2% b/w, Ca content 4.2% b/w, Na content 3.8% b/w ethanol synthetic rectified 98% (Chemopetrol Litvínov, a.s.)

redistilled $H_2O$ 1,2-monopropyleneglycol (Sigma)

sorbitol (Sigma)

isopropanol (Sigma)

Equipment propeller stirrer, 50 rpm sulphonation flask 1 l beaker 250 ml set of vibrating screens with mesh size 100, 150, 200, 250, 350, 500 $\mu$m counter-flow drier BINDER injection syringe 25 ml Procedure 10 g of MDOC Ca/Na salt and 90 g of redistilled $H_2O$ were introduced into the beaker, and dispersed using the propeller stirrer to obtain a colloidal solution.

A cogulating solution was prepared by dissolving 25 g of sorbitol and 25 g of monopropyleneglycol in 450 ml of 98% ethanol placed in the sulphonation flask. 1.0 g of mitoxanthron hydrochloride was placed into the 10 ml vial and dissolved in 5 g of redistilled water. The solution was then transferred into the sulphonation flask with ethanol under stirring.

The colloidal solution of MDOC was then gradually introduced into the sulphonation flask by being dropped, via the injection syringe, at a rate of 10 drops per minute. The microspheres were isolated from the coagulating bath by decantation, 250 ml of isopropanol were added and the microspheres were allowed to stay for 8 hours. The isopropanol was then removed by filtration and the microspheres were dried in the counter-flow drier at a temperature of 40° C. until the humidity content was reduced below 3% b/w. The dry microspheres were sieve-screened using the set of vibrating screens, and packaged into glass vials in amounts of 0.5 g each.

Indication

Microembolisation agent to achieve tissue necrotisation, e.g. in gynecological treatment of non-malignant tumours.

EXAMPLE N

Preparation of Rigid Foams from IMC-MDOC Complex Containing Gelatine

Material

IMC-MDOC complex—see Example 3

1,2-dihydroxypropane (Sigma)

gelatine, hydrolysed (Infusia, a.s.)

glycerol, medicinal (PhBs 1997)

redistilled $H_2O$

Equipment turbostirrer ULTRA TURAX (Janke-Kunkel)

sulphonation flask 1 l beaker 250 ml lyophiliser

Procedure 400 g IMC-MDOC complex, 100 g of gelatine, 100 g of 1,2-dihydroxypropane, 500 ml of redistilled water and 100 g of glycerol were introduced into the sulphonation flask. The mixture was heated up to 70° C. and homogenised using the propeller stirrer. Thereafter, the mixture was injected into suitably shaped moulds. After cooling down to room temperature, the moulds have been placed into the lyophiliser and the mass lyophilised. Tampons of the required shape were obtained in the form of a rigid flexible foam.

Indication

Suitable for use as biocompatible and fully resorbable nasal tampons.

EXAMPLE O

Preparation of Rigid Foams from IMC-MDOC Complex Containing Chitosan

Material
- IMC-MDOC complex—see Example 3
- 1,2-dihydroxypropane (Sigma)
- gelatine, hydrolysed (Infusia, a.s.)
- glutaraldehyde (Sigma)
- chitosan, degree of deacetylation 92% (Henkel)
- glycerol, medicinal (PhBs 1997)
- redistilled $H_2O$ Equipment
- turbostirrer ULTRA TURAX (Janke-Kunkel)
- sulphonation flask 1 l
- beaker 250 ml
- lyophiliser Procedure 400 g IMC-MDOC complex, 100 g of gelatine, 100 g of 1,2-dihydroxypropane, 500 ml of redistilled water and 100 g of glycerol were introduced into the sulphonation flask. The mixture was heated up to 70° C. and homogenised using the propeller stirrer. Subsequently, 20 g of chitosan were added, and the mixture was homogenised for another 5 minutes, Thereafter, 200 g of glutaraldehyde were added and the mixture was maintained 70° C. until the viscosity attained the value of 500 mPas. The mixture was then injected into suitably shaped moulds. After cooling down to room temperature, the moulds have been placed into the lyophiliser and the mass was lyophilised. Foamed sheets of the required shape consisting of an insoluble, highly absorbing, crosslinked foam were obtained.

Indication

Suitable for use as inner absorbing layers of biocompatible pads and plasters.

EXAMPLE P

Preparation of Microspheres from IMC-MDOC Complex Containing Platinum(II) Compounds Material
- MDOC (Ca/Na salt of PAGA), particle size 0.1–2.0 μm, specific surface area 86 $m^2/g$, COOH group content 22.2% b/w, Ca content 4.2% b/w, Na content 3.8% b/w
- ethanol synthetic rectified 98% (Chemopetrol Litvinov, a.s.)
- redistilled $H_2O$
- 1,2-dihydroxypropane (Sigma)
- polyacrylamide, 50% aqueous solution (Aldrich)
- glycerol, medicinal (PhBs 1997)

Equipment
- laboratory mixer, bottom agitated, 4000 rpm
- sulphonation flask 1 l
- injection syringe 25 ml Procedure A colloidal aqueous solution of an MDOC-chitosan-polyacrylamide complex containing 30% b/w of MDOC Ca/Na salt was dropped, via the injection syringe at a rate of 10 drops per minute, into a ethanol/glycerol/water system containing salts of bivalent platinum with two ammonia ($NH_3$) ligands. The microspheres formed, contained $(NH_3)_2Pt(II)$ groups, were isolated from the coagulating bath by decantation, washed with concentrated ethanol, and vacuum dried at 25° C.

Indication

Intraarterial (regional) chemotherapy of malignant tumours where diamoplatinum(II) complexes are indicated.

EXAMPLE Q

Preparation of Rigid Foams from IMC-MDOC Complex Containing Chitosan and Bestatin Material
- IMC-MDOC bestatin complex—see Example 11
- chitosan, degree of deacetylation 92% (Henkel)
- polyacrylamide, 50% aqueous solution (Aldrich)
- glycerol, medicinal (PhBs 1997)
- redistilled $H_2O$ Equipment
- turbostirrer ULTRA TURAX (Janke-Kunkel)
- sulphonation flask 1 l
- laboratory heater
- counter-flow drier BINDER Procedure Bestatin containing IMC-MDOC complex as prepared according to Example 11, glycerol, 25% aqueous solution of polyacrylamide, 3% solution of chitosan in acetic acid solution, and redistilled water were placed into the sulphonation flask in amounts such that the glycerol content in the system attains 30% b/w and that of the IMC-MDOC complex attains 0.1% b/w. The mixture was toroughly homogenised for 5 minutes using the turbostirrer, and n-pentane in an amount of 3%, calculated on the total volume basis, was added and dispersed into the system. Thereafter, the mixture was injected into suitably shaped moulds and dried to obtain flexible foamed sheets.

Indication

Suitable for use in preparation of embolisation agents, plasters and similar products.

EXAMPLE R

Preparation of Flat Textile-like Structures Containing MDOC and IMC-MDOC Complex with Bestatin Material
- cotton dressing pad
- MDOC (Ca/Na salt of PAGA), particle size 0.1–2.0 μm, specific surface area 86 $m^2/g$, COOH group content 22.2% b/w, Ca content 4.2% b/w, Na content 3.8% b/w
- IMC-MDOC bestatin complex—see Example 11
- ethanol synthetic rectified 98% (Chemopetrol Litvinov, a.s.)
- demineralised water 2 μS Equipment
- continuous spray-coating equipment Procedure A dispersion of MDOC Ca/Na containing 10% b/w IMC-MDOC bestatin complex prepared by the procedure according to Example 11 in 88.5% aqueous solution of ethanol was prepared within the storage tank of the spray coater. The dispersion was spray coated onto a cotton knitted pad to achieve an add-on within a range of area weights between 10 to 500 $g/m^2$. An impregnated flat textile-like structure was obtained on evaporating the aqueous ethanol.

Indication

Suitable for use in preparation of dressing materials for e.g. covering skin lesions after surgical removal of skin neoplasies.

The invention is not limited to the embodiments hereinbefore described which may be varied in detail.

What is claimed is:

1. A biocompatible intermolecular polymer complex of:
   an anionic component comprising a linear or branched polysaccharide chain wherein at least 5% of the basic structural units are those of glucuronic acid; and
   a non-protein cationic component comprising a linear or branched natural, semi-synthetic or synthetic oligomer or polymer.

2. A complex as claimed in claim 1 wherein the cationic component contains nitrogen that either carries a positive charge or wherein a positive charge is induced by contact with the polysaccharidic anionic component.

3. A complex as claimed in claim 2 wherein the cationic component is a member selected from the group consisting of an acrylamide, a methacrylamide and a copolymer of either.

4. A complex as claimed in claim 1 wherein the cationic component is a cationised natural polysaccharide.

5. A complex as claimed in claim 4 wherein the polysaccharide is a starch, cellulose or gum.

6. A complex as claimed in claim 1 wherein the cationic component is a synthetic or semi-synthetic polyamino acid.

7. A complex as claimed in claim 1 wherein the cationic component is a synthetic anti-fibrinolytic.

8. A complex as claimed in claim 1 wherein the cationic component is a natural or semi-synthetic peptide.

9. A complex as claimed in claim 1 wherein the cationic component is an aminoglucane or a modification thereof.

10. A complex as claimed in claim 1 wherein the anionic component comprises polyanhydroglucuronic acid(PAGA) or a salt thereof.

11. A complex as claimed in claim 10 wherein the polyanhydroglucuronic acid or salt thereof contains in its polymeric chain from 8 to 30 percent by weight of carboxyl groups, at least 80 percent by weight of these groups being uronic groups, at most 5 percent by weight of carbonyl groups, and at most 0.5 percent by weight of bound nitrogen.

12. A complex as claimed in claim 11 wherein the polyanhydroglucuronic acid or salt thereof contains in its polymeric chain at most 0.2 percent by weight of bound nitrogen.

13. A complex as claimed in claim 11 wherein the polymeric chain of the anionic component has a molecular mass of from $1 \times 10^3$ to $3 \times 10^5$ Daltons.

14. A complex as claimed in claim 11 wherein the content of carboxyl groups is in the range of from 12 to 26 percent by weight, at least 95 percent of these groups being uronic groups.

15. A complex as claimed in claim 11 wherein the anionic component contains at most 1 percent by weight of carbonyl groups.

16. A complex as claimed in claim 11 wherein each carbonyl group is a member selected from the group consisting of an intramolecular 2,6 hemiacetal, an intermolecular 2,6 hemiacetal, an intramolecular 3,6 hemiacetal, an intermolecular 3,6 hemiacetal, a 2,4 hemialdal, a C2 aldehyde and a C3 aldehyde.

17. A complex as claimed in claim 1 wherein the cationic component is gelatine.

18. A complex as claimed in claim 1 wherein the cationic component is chitosan.

19. A complex as claimed in claim 2 wherein the cationic component is a member selected from the group consisting of a polyacrylamide, a copolymer of hydroxyethylmethacrylate and hydroxypropylmethacrylamide, a copolymer of acrylamide, butylacrylate, maleic anhydride and methylmethacrylate, and a copolymer of acrylamide, butylacrylate and methylmethacrylate.

20. A complex as claimed in claim 5 wherein the gum is guargumhydroxypropyltriammonium chloride.

21. A complex as claimed in claim 1 wherein the cationic component is a member selected from the group consisting of polylysin, polyarginin, and $\alpha,\beta$-poly-[N-(2-hydroxyethyl)-DL-aspartamide].

22. A complex as claimed in claim 7 wherein the synthetic anti-fibrinolytic is a hexadimethrindibromide (polybren).

23. A complex as claimed in claim 8 wherein the peptide is an optionally modified member selected from the group consisting of protamine, gelatine and fibrinopeptide.

24. A complex as claimed in claim 1 wherein the cationic component is fractionated chitin or its de-acetylated derivative chitosan.

25. A complex as claimed in claim 9 wherein the aminoglucane is of microbial origin or is isolated from an arthropod shell.

26. A complex as claimed in claim 13 wherein the molecular mass of the polymeric chain of the anionic component ranges from $5 \times 10^3$ to $1.5 \times 10^5$ Daltons.

27. A complex as claimed in claim 2 wherein the cationic component is a synthetic biocompatible nitrogen-containing oligomer or polymer.

28. A complex as claimed in claim 10 wherein the cationic component comprises chitosan.

29. A complex as claimed in claim 1 wherein the cationic component is a member selected from the group consisting of:

an acrylamide;

a methacrylamide;

an acrylamide copolymer;

a methacrylamide copolymer;

a cationised natural polysaccharide;

a synthetic polyamino acid;

a synthetic anti-fibrinolytic;

a natural peptide;

a semi-synthetic peptide; and an aminoglucane.

30. A complex as claimed in claim 29 wherein the cationic component is a member selected from the group consisting of a polyacrylamide, a copolymer of hydroxyethyl-methacrylate and hydroxypropyl-methacrylate, a copolymer of acrylamide, butyl acrylate and maleic anhydride, and a copolymer of acrylamide, butylacrylate and methyl-methacrylate.

31. A complex as claimed in claim 29 wherein the anionic component comprises polyanhydroglucuronic acid, which contains in its polymeric chain from 8 to 30 percent by weight of carboxyl groups, at least 80 percent by weight of these groups being uronic groups, at most 5 percent by weight of carbonyl groups, and at most 0.5 percent by weight of bound nitrogen, or a salt thereof.

32. A complex as claimed in claim 31 wherein the polyanhydroglucuronic acid or salt thereof contains in its polymeric chain at most 0.2 percent by weight of bound nitrogen.

33. A complex as claimed in claim 31 wherein the anionic component contains at most 1 percent by weight of carbonyl groups.

* * * * *